United States Patent
Serino et al.

(10) Patent No.: US 11,939,213 B2
(45) Date of Patent: Mar. 26, 2024

(54) PROGRAMMABLE STRUCTURAL BUILDING BLOCKS

(71) Applicant: RAYTHEON COMPANY, Waltham, MA (US)

(72) Inventors: Anthony Serino, Northborough, MA (US); Jacob Beal, Iowa City, IA (US); Miles T. Rogers, Watertown, MA (US)

(73) Assignee: RAYTHEON COMPANY, Waltham, MA (US)

( * ) Notice: Subject to any disclaimer, the term of this patent is extended or adjusted under 35 U.S.C. 154(b) by 659 days.

(21) Appl. No.: 17/129,197

(22) Filed: Dec. 21, 2020

(65) Prior Publication Data

US 2022/0194785 A1 Jun. 23, 2022

(51) Int. Cl.
*C30B 29/58* (2006.01)
*B81C 1/00* (2006.01)
*B82Y 5/00* (2011.01)
*B82Y 40/00* (2011.01)

(52) U.S. Cl.
CPC .. *B81C 1/00031* (2013.01); *B81C 2201/0149* (2013.01); *B82Y 5/00* (2013.01); *B82Y 40/00* (2013.01)

(58) Field of Classification Search
CPC ............... C30B 29/58; B81C 1/00031; B81C 2201/0149; B81Y 5/00; B82Y 40/00
See application file for complete search history.

(56) References Cited

U.S. PATENT DOCUMENTS

| | | | |
|---|---|---|---|
| 9,617,392 B2 | 4/2017 | Schaus et al. | |
| 9,765,341 B2 | 9/2017 | Bachelet et al. | |
| 10,380,479 B2 | 8/2019 | Chang et al. | |
| 10,640,826 B2 | 5/2020 | Church et al. | |
| 11,065,345 B2* | 7/2021 | Hawthorne | A61K 47/6929 |
| 11,560,644 B2* | 1/2023 | Stoddart | C30B 29/54 |
| 2018/0208456 A1 | 7/2018 | Santos et al. | |
| 2018/0208466 A1* | 7/2018 | Noyes | B82Y 30/00 |
| 2020/0179531 A1 | 6/2020 | Hawthorne et al. | |

OTHER PUBLICATIONS

Zhang et al., Complex Archimedean tiling self-assembled from DNA nanostructures: ACS Journal American Chemical Society 7458-7462 May 2013.*

(Continued)

*Primary Examiner* — Robert M Kunemund
(74) *Attorney, Agent, or Firm* — CANTOR COLBURN LLP (57) ABSTRACT

A structural molecular building block is provided and includes first structural molecules arranged in a three-dimensional structure and second structural molecules. Each of the second structural molecules is attached at a first region thereof to one of the first structural molecules to form the three-dimensional structure into a tessellating molecular building block and has a second region thereof for connection to a corresponding structural molecule of an additional tessellating molecular building block. The second structural molecules facilitate tessellation of the tessellating molecular building block with additional tessellating molecular building blocks to encourage growth of a macroscopic crystal.

20 Claims, 6 Drawing Sheets

(56) References Cited

OTHER PUBLICATIONS

Zhang et al., "Self assembly of 3d DNA Crystal structure with rationally designed six fold symmetry", Amgew Chem Int Ed 2018 12504-12507.*

Hong et al., "Layered-Crossover Tiles with Precisely Tunable Angles for 2D and 3D DNA Crystal Engineering" Journal of the American Chemical Society, vol. 140, No. 44 (Nov. 7, 2018) pp. 14670-14676.

ISR/WO, dated Mar. 18, 2022, RAY0474PCT.

Li et al., "Making Engineered 3D DNA Crystals Robust" Journal of the American Chemical Society, vol. 141, No. 40 (Oct. 9, 2019) Abstract Only (7 pages).

Ong et al., "Programmable Self-Assembly of Three-Dimensional Nanostructures from 10,000 Unique Components" Nature, vol. 552, No. 7683 (Dec. 7, 2017) Abstract Only (13 pages).

Yao et al., "Meta-DNA Structures" Nature Chemistry, Nature Publishing Group UK, London, vol. 12, No. 11 (Sep. 7, 2020) Abstract Only (13 pages).

Zhang et al., "Self-Assembly of a 3D DNA Crystal Structure with Rationally Designed Six-Fold Symmetry" Angewandte Chemie International Edition, vol. 57, No. 38 (Sep. 17, 2018) Abstract Only (1 page).

Zheng et al., "From Molecular to Macroscopic via the Rational Design of a Self-Assembled 3D DNA Crystal" Nature, Nature Publishing Group UK, London, vol. 461, No. 7260 (Sep. 3, 2009) Abstract Only (9 pages).

* cited by examiner

PROGRAMMABLE STRUCTURAL BUILDING BLOCKS

BACKGROUND

The present disclosure relates to building blocks and, in particular, to programmable structural building blocks.

Nanotechnology is often defined as the study of materials and devices with features on a very small scale (e.g., below about ~100 nanometers). DNA nanotechnology, specifically, is an example of bottom-up molecular self-assembly, in which molecular components spontaneously organize into stable structures and where the particular form of these structures can be induced by the physical and chemical properties of the components selected by the designers. In DNA nanotechnology, the component materials are strands of nucleic acids such as DNA. These strands are often synthetic and are typically used outside the context of a living cell. DNA is often well-suited to nanoscale construction because the binding between two nucleic acid strands depends on simple base pairing rules that are well understood and form the specific nanoscale structure of the nucleic acid double helix. These qualities make the assembly of nucleic acid structures easy to control through nucleic acid design.

SUMMARY

According to an aspect of the disclosure, a structural molecular building block is provided and includes first structural molecules arranged in a three-dimensional structure and second structural molecules. Each of the second structural molecules is attached at a first region thereof to one of the first structural molecules to form the three-dimensional structure into a tessellating molecular building block and has a second region thereof for connection to a corresponding structural molecule of an additional tessellating molecular building block. The second structural molecules facilitate tessellation of the tessellating molecular building block with additional tessellating molecular building blocks to encourage growth of a macroscopic crystal.

In accordance with additional or alternative embodiments, the first and second structural molecules include at least one of DNA molecules, RNA molecules and elongate proteins and the three-dimensional structure includes at least one of a linear structure, an angular structure and a regular or irregular polygonal structure with at least length-wise and width-wise components respectively formed by the first structural molecules.

In accordance with additional or alternative embodiments, the first and second structural molecules include DNA molecules and the three-dimensional structure includes at least one of a linear structure, an angular structure and a regular or irregular polygonal structure with at least length-wise and width-wise components respectively formed by the first structural molecules.

In accordance with additional or alternative embodiments, the second structural molecules extend outwardly from the three-dimensional structure in one or more of first, second and third transverse dimensions to facilitate the tessellation of the tessellating molecular building block with the additional tessellating molecular building blocks in the one or more of the first, second and third transverse dimensions.

According to an aspect of the disclosure, a method of assembling structural molecular building blocks into a macroscopic crystal is provided and includes forming multiple types of tessellating molecular building blocks. Each type of the tessellating molecular building blocks includes first structural molecules arranged in a three-dimensional structure and second structural molecules and each of the second structural molecules is attached at a first region thereof to one of the first structural molecules and has a second region thereof for connection to a corresponding structural molecule of an additional tessellating molecular building block of a same or one or more different types. The method further includes mixing the tessellating molecular building blocks of a type with additional tessellating molecular building blocks of the same or the one or more different types to encourage growth of a macroscopic crystal.

In accordance with additional or alternative embodiments, the first and second structural molecules include at least one of DNA molecules, RNA molecules and elongate proteins and the three-dimensional structure includes at least one of a linear structure, an angular structure and a regular or irregular polygonal structure with at least length-wise and width-wise components respectively formed by the first structural molecules.

In accordance with additional or alternative embodiments, the first and second structural molecules include DNA molecules and the three-dimensional structure includes at least one of a linear structure, an angular structure and a regular or irregular polygonal structure with at least length-wise and width-wise components respectively formed by the first structural molecules.

In accordance with additional or alternative embodiments, the second structural molecules extend outwardly from the three-dimensional structure in one or more of first, second and third transverse dimensions and facilitate the tessellation of the tessellating molecular building blocks of the type with the additional tessellating molecular building blocks of the same or the one or more different types in the one or more of the first, second and third transverse dimensions.

In accordance with additional or alternative embodiments, the mixing includes introducing the tessellating molecular building blocks of the type with the additional tessellating molecular building blocks of the same or the one or more different types in a solution.

In accordance with additional or alternative embodiments, the introducing includes replacing the additional tessellating molecular building blocks of the same or the one or more different types with different additional tessellating molecular building blocks of the same or the one or more different types to encourage growth of a complex macroscopic crystal.

In accordance with additional or alternative embodiments, the introducing includes applying external forces to the solution to encourage growth of a complex macroscopic crystal.

According to an aspect of the disclosure, a method of assembling structural molecular building blocks into a macroscopic crystal is provided and includes laying down a substrate comprising posts of structural molecules and forming multiple types of tessellating molecular building blocks. Each type of the tessellating molecular building blocks includes first structural molecules arranged in a three-dimensional structure and second structural molecules and each of the second structural molecules is attached at a first region thereof to one of the first structural molecules and has a second region thereof for connection to a post or to a corresponding structural molecule of an additional tessellating molecular building block of a same or one or more different types. The method further includes mixing the tessellating molecular building blocks of a type with the substrate and with additional tessellating molecular building blocks of the same or the one or more different types to encourage growth of a macroscopic crystal on the substrate.

In accordance with additional or alternative embodiments, the first and second structural molecules include at least one of DNA molecules, RNA molecules and elongate proteins and the three-dimensional structure includes at least one of a linear structure, an angular structure and a regular or irregular polygonal structure with at least length-wise and width-wise components respectively formed by the first structural molecules.

In accordance with additional or alternative embodiments, the first and second structural molecules include DNA molecules and the three-dimensional structure includes at least one of a linear structure, an angular structure and a regular or irregular polygonal structure with at least length-wise and width-wise components respectively formed by the first structural molecules.

In accordance with additional or alternative embodiments, the second structural molecules extend outwardly from the three-dimensional structure in one or more of first, second and third transverse dimensions and facilitate the tessellation of the tessellating molecular building blocks of the type with the additional tessellating molecular building blocks of the same or the one or more different types in the one or more of the first, second and third transverse dimensions.

In accordance with additional or alternative embodiments, the mixing includes introducing the tessellating molecular building blocks of the type with the substrate and the additional tessellating molecular building blocks of the same or the one or more different types in a solution.

In accordance with additional or alternative embodiments, the introducing includes replacing the additional tessellating molecular building blocks of the same or the one or more different types with different additional tessellating molecular building blocks of the same or the one or more different types to encourage growth of a complex macroscopic crystal on the substrate.

In accordance with additional or alternative embodiments, the introducing includes applying external forces to the solution to encourage growth of a complex macroscopic crystal on the substrate.

In accordance with additional or alternative embodiments, the introducing includes masking the substrate to encourage growth of a complex macroscopic crystal on the substrate.

In accordance with additional or alternative embodiments, the method further includes removing the macroscopic crystal from the substrate and repeating the mixing to encourage growth of a second macroscopic crystal on the substrate.

Additional features and advantages are realized through the techniques of the present disclosure. Other embodiments and aspects of the disclosure are described in detail herein and are considered a part of the claimed technical concept. For a better understanding of the disclosure with the advantages and the features, refer to the description and to the drawings.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

DETAILED DESCRIPTION

It has been seen that engineering with structural DNA is often limited in scale and application. Thus, as will be described below, a novel design of structural molecules (e.g., DNA, RNA, elongate proteins, etc.) is provided for use as precise, programmable building materials. This could enable structural molecules to scale by orders of magnitude to significantly larger dimensions than currently employed (traditionally faulty beyond micron-scale), which would open many future applications in multiple industries.

Figure 1:
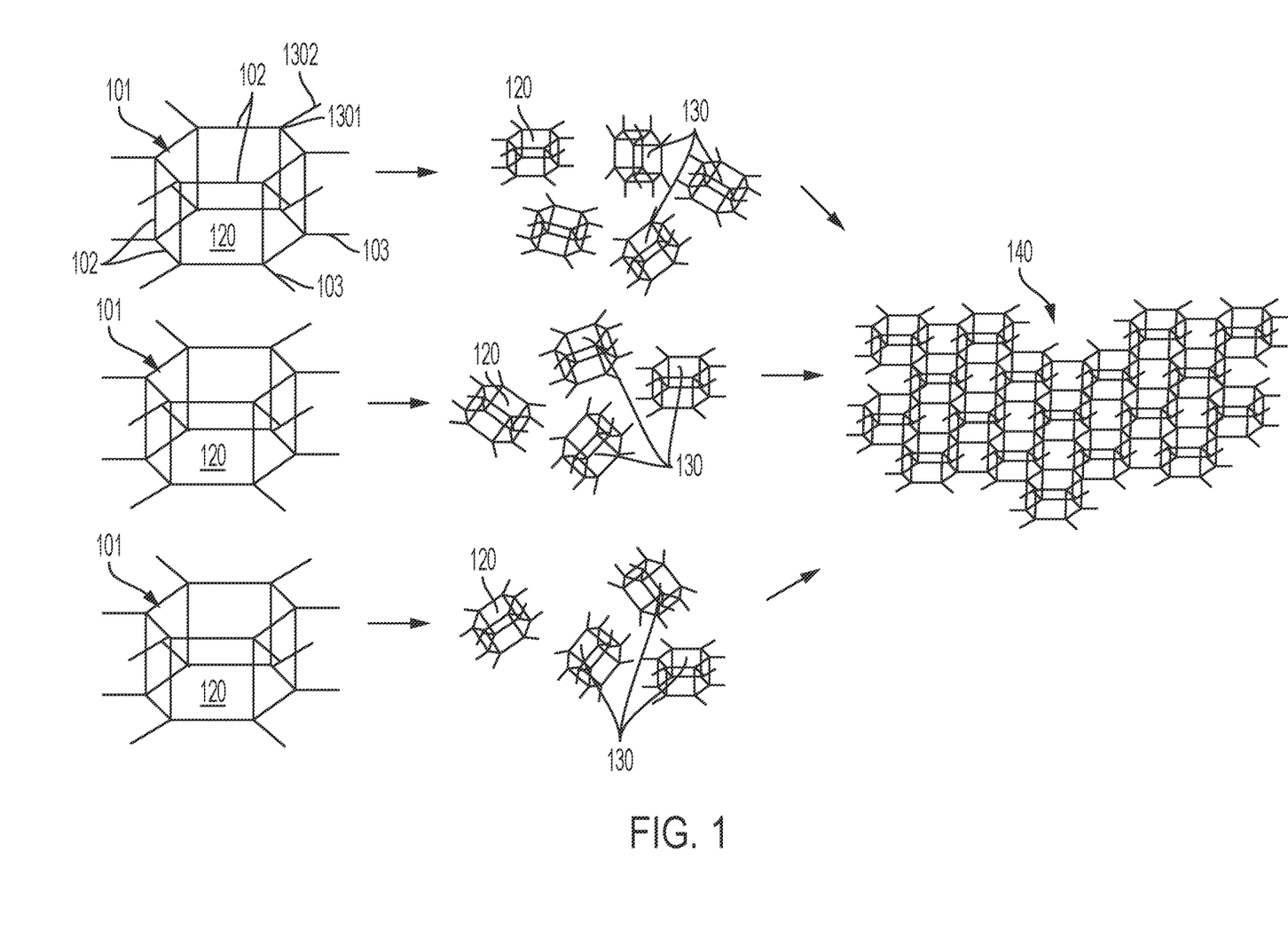
FIG. 1 is a schematic illustrating of structural molecular building blocks forming a macroscopic crystal in accordance with embodiments.

With reference to FIG. 1, a structural molecular building block 101 is provided. As shown in FIG. 1, the structural molecular building block 101 includes first structural molecules 102 arranged in a three-dimensional structure 110 and second structural molecules 103. Each of the second structural molecules 103 has a first end or region 1301 and a second end or region 1032 and is attached at the first end or region 1031 thereof to one or more of the first structural molecules 102. This attachment forms the three-dimensional structure 110 into a tessellating molecular building block 120. The second end or region 1032 of each of the second structural molecules 103 is connectable to a corresponding structural molecule of an additional tessellating molecular building block 130. The second structural molecules 103 thus facilitate tessellation of the tessellating molecular building block 120 with additional tessellating molecular building blocks 130 to encourage growth of a macroscopic crystal 140.

In accordance with embodiments, the first end or region 1301 of each second structural molecule 103 can be at or proximate to a first distal end of the second structural molecule 103 and the second end or region 1302 of each second structural molecule 103 can be at or proximate to a second distal end of the second structural molecule 103, which is opposite the first distal end. The first end or region 1301 can extend along a significant fraction of a length of the second structural molecule 103 from the first distal end and the second end or region 1302 can similarly extend along a significant fraction of the length of the second structural molecule 103 from the second distal end. As used herein, the first end or region 1301 can refer to the portion of the second structural molecule 103 that is intended to bind with its complement on the three-dimensional structure 110 and the second end or region 1302 can refer to the portion of the second structural molecule 103 that is intended to bind with its complement on the corresponding structural molecule of an additional tessellating molecular building block 130.

In accordance with embodiments, the first and second structural molecules 102 and 103 can include or be provided as at least one of DNA molecules, RNA molecules and elongate proteins. In these or other cases, the three-dimensional structure 110 can include or be provided as at least one of a linear structure (such as a straight or curved line of molecules), an angular structure (such as an angled line of molecules) and a regular or irregular polygonal structure (such as a ring of molecules). The linear structure, the angular structure and the regular or irregular polygonal structure can have length-wise and width-wise components respectively formed by the first structural molecules 102 such as where the first structural molecules 102 are substantially in a same plane with one another. Alternatively or additionally, the linear structure, the angular structure and the regular or irregular polygonal structure can have length-wise, width-wise and height-wise components respectively formed by the first structural molecules 102 such as where the first structural molecules 102 are in multiple planes with one another.

The second structural molecules 103 can extend outwardly from the three-dimensional structure 110 in one or more of first, second and third transverse dimensions (i.e., the length-wise, the width-wise and the height-wise dimensions) to facilitate the tessellation of the tessellating molecular building block 120 with the additional tessellating molecular building blocks 130 in the one or more of the first, second and third transverse dimensions.

For purposes of clarity and brevity, the details of FIG. 1, the text accompanying FIG. 1 and the following description will all relate to the exemplary case in which the first and second structural molecules 102 and 103 are DNA molecules and the three-dimensional structure 110 is a hexagonal body with two substantially flat rings formed by six first structural molecules 102 and six connectors between corresponding vertices that are also formed by first structural molecules 102.

In addition, for purposes of clarity and brevity, the details of FIG. 1, the text accompanying FIG. 1 and the following description will all relate to the exemplary case in which the second structural molecules 103 extend outwardly from the three-dimensional structure 110 in the first or second dimensions (i.e., the length-wise or the width-wise dimensions) to facilitate the tessellation of the tessellating molecular building block 120 with the additional tessellating molecular building blocks 130 in the first or second transverse dimensions or in the third transverse dimension (i.e., the height-wise dimension) to facilitate the tessellation of the tessellating molecular building block 120 with the additional tessellating molecular building blocks 130 in the third transverse dimension.

As such, the macroscopic crystal 140 can have a hexagonal lattice or honeycomb configuration with multiple layers and multiple tessellating molecular building blocks in each layer and can be formed without assistance in solution over time without small scale human or mechanical interaction. Therefore, the macroscopic crystal 140 can have a relatively large scale and be grown from relatively very small-scale components.

It is to be understood that the tessellation of the tessellating molecular building block 120 with the additional tessellating molecular building blocks 130 is achieved by the interaction and connectability of the second end or region 1302 of each second structural molecule 103 with the corresponding structural molecule of the additional tessellating molecular building block 130. In particular, where the second structural molecules 103 are DNA molecules, distal ends of the second structural molecules 103 can be designed to connect to distal ends of one or more types of other predefined DNA molecules. Thus, in a solution of the tessellating molecular building blocks 103 where the second structural molecules 103 are connectable with each other, the tessellating molecular building blocks 103 will tessellate and form the macroscopic crystal 140 as a unitary homogenous body from multiple tessellating molecular building blocks 103 all of the same type.

Alternatively, the macroscopic crystal 140 can be formed as a complex unitary heterogenous body from multiple tessellating molecular building blocks 103 of different types.

For example, a solution of multiple different types of the tessellating molecular building blocks 103 can be provided in which the second structural molecules 103 of one type of the tessellating molecular building blocks 103 are connectable with second structural molecules of two other types of the tessellating molecular building blocks 103. In such a case, the macroscopic crystal 140 can be formed from the tessellating molecular building blocks 103 of the one type being connected with the tessellating molecular building blocks 103 of the two other types.

Figure 2:
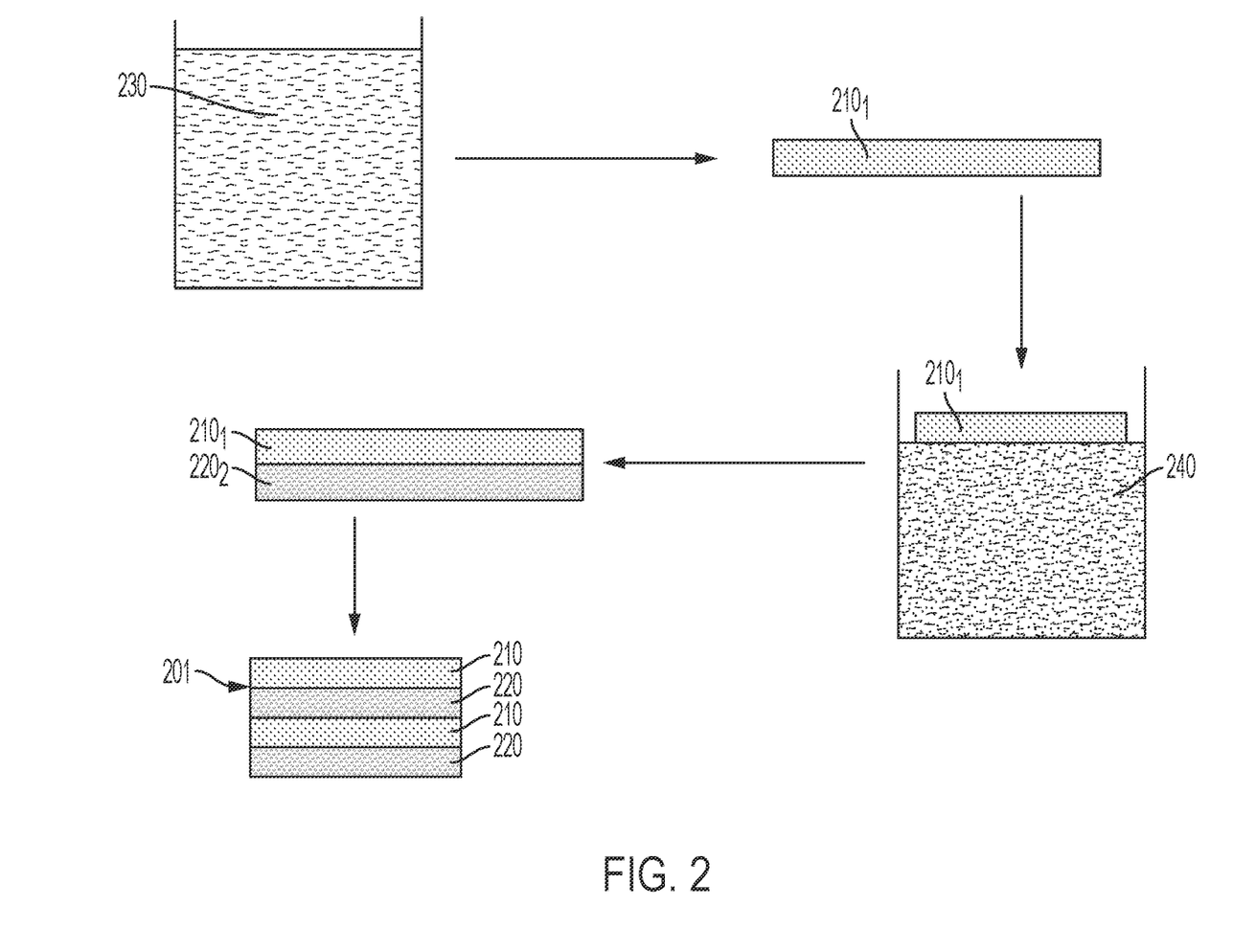
FIG. 2 is a schematic illustration of structural molecular building blocks forming a macroscopic crystal with patterned stripes in accordance with embodiments.
Figure 3:
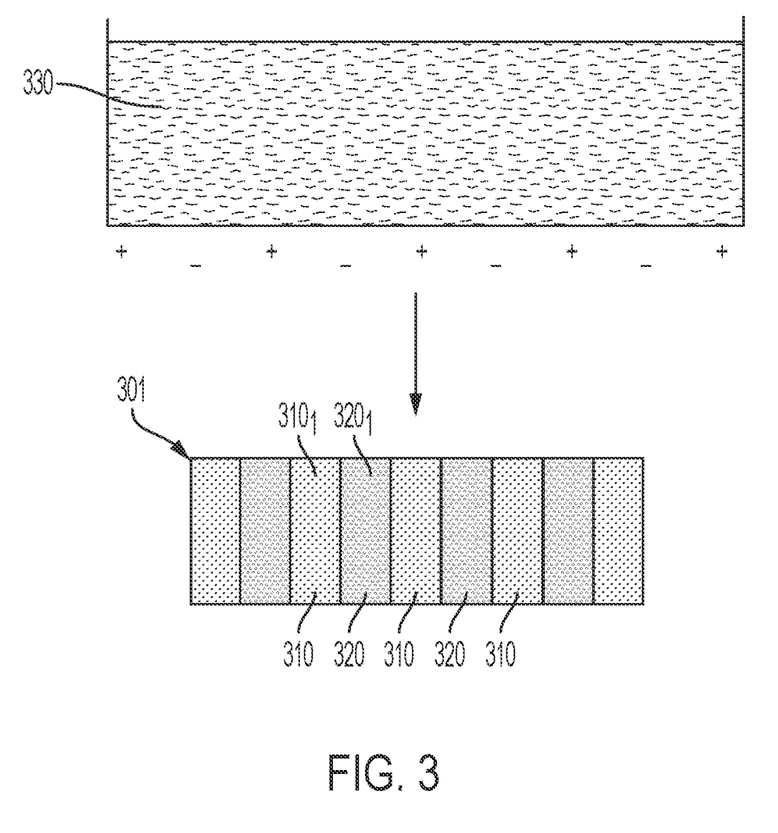
FIG. 3 is a schematic illustration of structural molecular building blocks forming a macroscopic crystal with patterned stripes in accordance with embodiments.

As a further example, with reference to FIGS. 2 and 3, the complexity of the macroscopic crystal 140 can be arrived at by use of macroscopic or large-scale interactions with the solution. Such macroscopic or large-scale interactions can include introducing multiple types of the tessellating molecular building blocks 103 into the solution sequentially to arrive at particular tessellating patterns (see FIG. 2) and/or applying external forces (e.g., magnetic or electrical fields) to the solution to arrive at particular tessellating patterns (see FIG. 3).

As shown in FIG. 2, the particular tessellating pattern may be a striped pattern 201 in which each one set of stripes 210 includes tessellating molecular building blocks 103 of a first type which are connectable to each other or to tessellating molecular building blocks 103 of a second type and the other set of stripes 220 includes the tessellating molecular building blocks 103 of the second type, which are also connectable with each other. In this case, a first solution 230 might be provided in which only the tessellating molecular building blocks 103 of the first type are present so that a resulting macroscopic crystal grows as an initial stripe $210_1$. Next, a side of the initial stripe $210_1$ is immersed in a second solution 240 in which only the tessellating molecular building blocks 103 of the second type are present so that the resulting macroscopic crystal grows a secondary stripe $220_2$ at an edge of the initial stripe $210_1$. This process can be repeated by repeated reuses of the first and second solutions 230 and 240 in turn.

As shown in FIG. 3, the particular tessellating pattern may again be a striped pattern 301 in which each one set of stripes 310 includes tessellating molecular building blocks 103 of a first type which are connectable to each other or to tessellating molecular building blocks 103 of a second type and the other set of stripes 320 includes the tessellating molecular building blocks 103 of the second type, which are also connectable with each other. In this case, a solution 330 might be provided in which the tessellating molecular building blocks 103 of the first and second types are present and exposed to stripes of magnetic fields (+/−) that are more attractive to either the first or the second types. Here, a resulting macroscopic crystal grows with stripes $310_1$ and $320_1$ as the tessellating molecular building blocks 103 of the first and second types tend to congregate proximate to the magnetic fields to which they are attracted.

Figure 4:
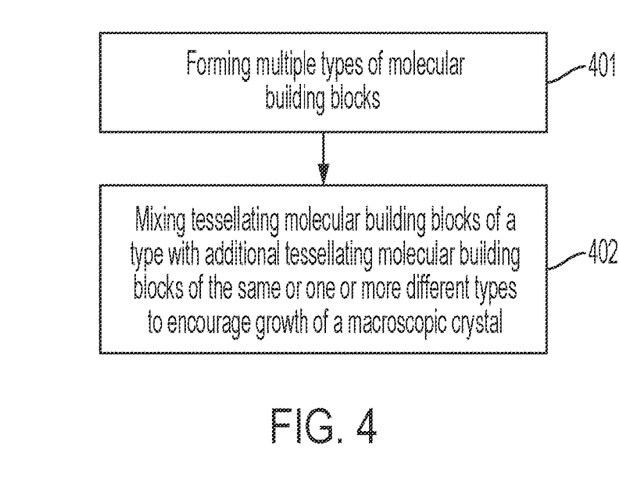
FIG. 4 is a flow diagram illustrating a method of assembling structural molecular building blocks into a macroscopic crystal in accordance with embodiments.

With reference to FIG. 4, a method of assembling structural molecular building blocks into a macroscopic crystal as described above is provided and includes forming multiple types of tessellating molecular building blocks (401), where each type of the tessellating molecular building blocks include first structural molecules arranged in a three-dimensional structure and second structural molecules, and where each of the second structural molecules is attached at a first end or region thereof to one of the first structural molecules and has a second end or region thereof for connection to a corresponding structural molecule of an additional tessellating molecular building block of a same or one or more different types. The method further includes mixing the tessellating molecular building blocks of a type with additional tessellating molecular building blocks of the same or the one or more different types to encourage growth of a macroscopic crystal (402).

As described above, the mixing of operation 402 can include introducing the tessellating molecular building blocks of the type with the additional tessellating molecular building blocks of the same or the one or more different types in a solution. In addition, the introducing can include replacing the additional tessellating molecular building blocks of the same or the one or more different types with different additional tessellating molecular building blocks of the same or the one or more different types to encourage growth of a complex macroscopic crystal and/or applying external forces to the solution to encourage growth of a complex macroscopic crystal.

Figure 5:
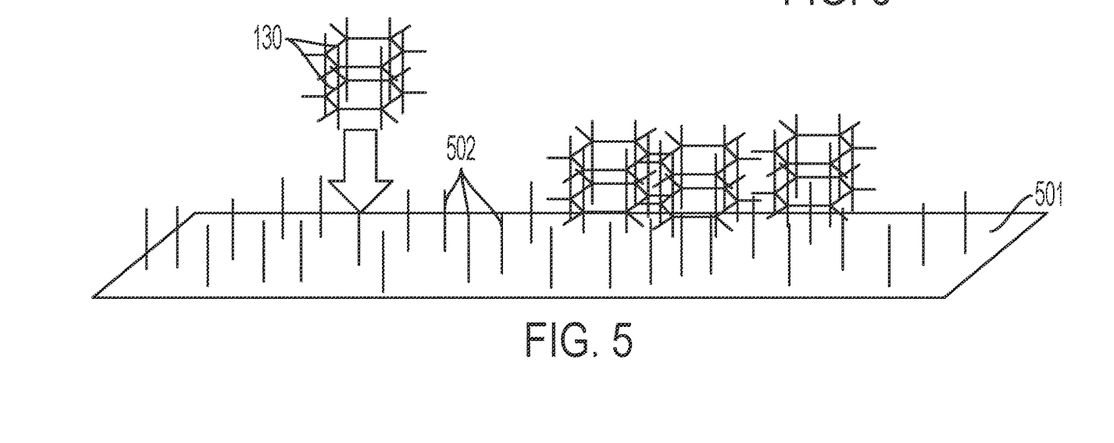
FIG. 5 is a perspective view of a substrate with posts of structural molecules in accordance with embodiments.
Figure 6:
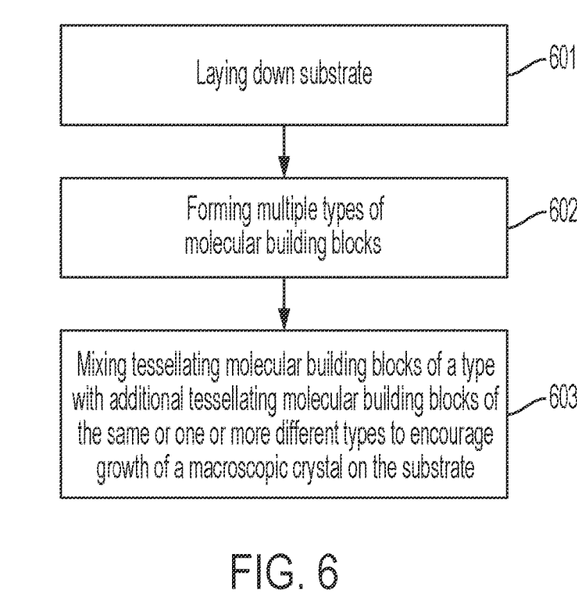
FIG. 6 is a flow diagram illustrating a method of assembling structural molecular building blocks into a macroscopic crystal on the substrate of FIG. 5 in accordance with embodiments.

With reference to FIGS. 5 and 6, a method of assembling structural molecular building blocks into a macroscopic crystal as described above is provided and includes laying down a substrate 501 that includes posts 502 of structural molecules, such as DNA molecules (601), forming multiple types of tessellating molecular building blocks as in operation 401 of FIG. 4 (602) where the second end or region of each of the second structural molecules is connectable to a post 502 or to a corresponding structural molecule of an additional tessellating molecular building block of a same or one or more different types. The method further includes mixing the tessellating molecular building blocks of a type with the substrate and with additional tessellating molecular building blocks of the same or the one or more different types to encourage growth of a macroscopic crystal on the substrate (603).

As described above, the mixing of operation 402 can include introducing the tessellating molecular building blocks of the type with the substrate 501 and the additional tessellating molecular building blocks of the same or the one or more different types in a solution. In addition, the introducing can include replacing the additional tessellating molecular building blocks of the same or the one or more different types with different additional tessellating molecular building blocks of the same or the one or more different types to encourage growth of a complex macroscopic crystal, applying external forces to the solution to encourage growth of a complex macroscopic crystal and/or masking the substrate 501.

Figure 7:
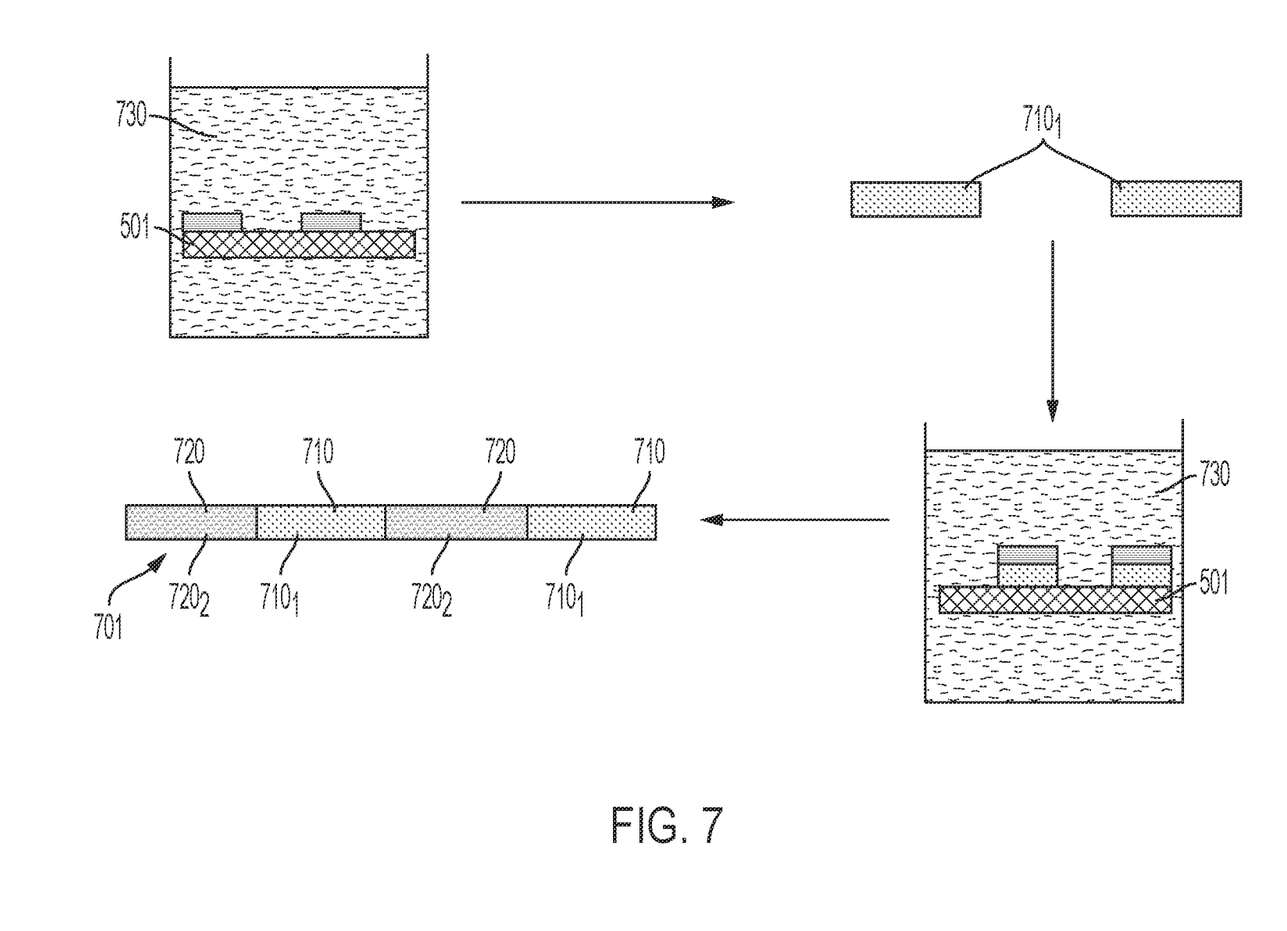
FIG. 7 is a schematic illustration of structural molecular building blocks forming a macroscopic crystal with patterned stripes on the substrate of FIG. 5 in accordance with embodiments.

With reference to FIG. 7, a particular tessellating pattern may again be a striped pattern 701 in which each set of stripes 710 includes tessellating molecular building blocks 103 of a first type which are connectable to each other or to tessellating molecular building blocks 103 of a second type and the other set of stripes 720 includes the tessellating molecular building blocks 103 of the second type, which are also connectable with each other. In this case, a solution 730 might be provided in which the substrate 501 is present with only the tessellating molecular building blocks 103 of the first type and all of the posts 502 (see FIG. 5) of the substrate 501 are connectable with the first and second types of the tessellating molecular blocks 103. Here, if the regions of the stripes 720 are masked, resulting macroscopic crystals grow as initial stripes $710_1$ from the connections of the tessellating molecular blocks 103 of the first type with each other and the exposed posts 502 of the substrate 501. Next, if the regions of the stripes 720 are unmasked and the regions of the stripes 710 are masked, the resulting macroscopic crystals continue to grow in the solution 730 as secondary stripes $720_2$ from the connections of the tessellating molecular blocks 103 of the second type with each other, the exposed posts 502 of the substrate 501 and exposed portions of the initial stripes $710_1$.

Figure 8:
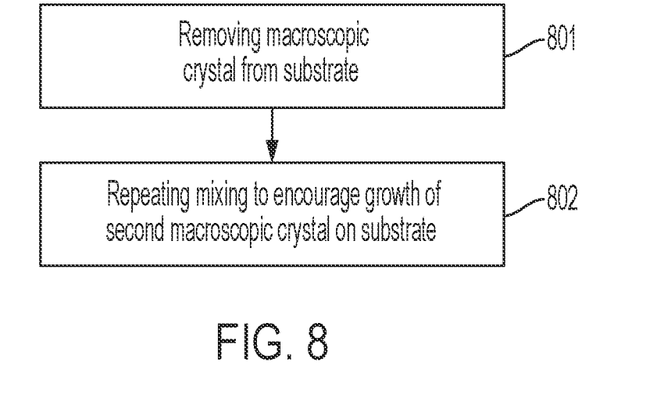
FIG. 8 is a flow diagram illustrating additional operations of the method of assembling structural molecular building blocks into a macroscopic crystal on the substrate of FIGS. 5 and 6 in accordance with embodiments.

With reference to FIG. 8, the method of FIG. 6 can further include removing the macroscopic crystal from the substrate (801) and repeating the mixing to encourage growth of a second macroscopic crystal on the substrate (802). These additional operations can be continued as long as the substrate remains viable to produce a number of the macroscopic crystals from the substrate, which is essentially acting as a template in these or other cases.

Technical effects and benefits of the present disclosure are the provision of structural molecules (e.g., DNA, RNA, elongate proteins, etc.) for use as precise, programmable building materials to enable crystal growth with scaling to dimensions that are significantly larger than molecular dimensions.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the technical concepts in the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

While the preferred embodiments to the disclosure have been described, it will be understood that those skilled in the art, both now and in the future, may make various improvements and enhancements which fall within the scope of the claims which follow. These claims should be construed to maintain the proper protection for the disclosure first described.

What is claimed is:
1. A structural molecular building block, comprising:
a substrate comprising posts of structural molecules;
first structural molecules arranged in a three-dimensional structure; and
second structural molecules, wherein:
each of the second structural molecules is attached at a first region thereof to one of the first structural molecules to form the three-dimensional structure into a tessellating molecular building block and has a second region thereof for connection to a post or to a corre- sponding structural molecule of an additional tessellating molecular building block, and
the second structural molecules facilitate tessellation of the tessellating molecular building block with additional tessellating molecular building blocks to encourage growth of a macroscopic crystal.

2. The structural molecular building block according to claim 1, wherein:
the first and second structural molecules comprise at least one of DNA molecules, RNA molecules and elongate proteins, and
the three-dimensional structure comprises at least one of a linear structure, an angular structure and a regular or irregular polygonal structure with at least length-wise and width-wise components respectively formed by the first structural molecules.

3. The structural molecular building block according to claim 1, wherein:
the first and second structural molecules comprise DNA molecules, and
the three-dimensional structure comprises at least one of a linear structure, an angular structure and a regular or irregular polygonal structure with at least length-wise and width-wise components respectively formed by the first structural molecules.

4. The structural molecular building block according to claim 1, wherein the second structural molecules extend outwardly from the three-dimensional structure in one or more of first, second and third transverse dimensions to facilitate the tessellation of the tessellating molecular building block with the additional tessellating molecular building blocks in the one or more of the first, second and third transverse dimensions.

5. A method of assembling structural molecular building blocks into a macroscopic crystal, the method comprising:
a substrate comprising posts of structural molecules;
forming multiple types of tessellating molecular building blocks,
each type of the tessellating molecular building blocks comprising first structural molecules arranged in a three-dimensional structure and second structural molecules,
wherein each of the second structural molecules is attached at a first region thereof to one of the first structural molecules and has a second region thereof for connection to a post or to a corresponding structural molecule of an additional tessellating molecular building block of a same or one or more different types; and
mixing the tessellating molecular building blocks of a type with additional tessellating molecular building blocks of the same or the one or more different types to encourage growth of a macroscopic crystal.

6. The method according to claim 5, wherein:
the first and second structural molecules comprise at least one of DNA molecules, RNA molecules and elongate proteins, and
the three-dimensional structure comprises at least one of a linear structure, an angular structure and a regular or irregular polygonal structure with at least length-wise and width-wise components respectively formed by the first structural molecules.

7. The method according to claim 5, wherein:
the first and second structural molecules comprise DNA molecules, and
the three-dimensional structure comprises at least one of a linear structure, an angular structure and a regular or irregular polygonal structure with at least length-wise and width-wise components respectively formed by the first structural molecules.

8. The method according to claim 5, wherein the second structural molecules extend outwardly from the three-dimensional structure in one or more of first, second and third transverse dimensions and facilitate the tessellation of the tessellating molecular building blocks of the type with the additional tessellating molecular building blocks of the same or the one or more different types in the one or more of the first, second and third transverse dimensions.

9. The method according to claim 5, wherein the mixing comprises introducing the tessellating molecular building blocks of the type with the additional tessellating molecular building blocks of the same or the one or more different types in a solution.

10. A method of assembling structural molecular building blocks into a macroscopic crystal, the method comprising:
forming multiple types of tessellating molecular building blocks,
each type of the tessellating molecular building blocks comprising first structural molecules arranged in a three-dimensional structure and second structural molecules,
wherein each of the second structural molecules is attached at a first region thereof to one of the first structural molecules and has a second region thereof for connection to a corresponding structural molecule of an additional tessellating molecular building block of a same or one or more different types; and
mixing the tessellating molecular building blocks of a type with additional tessellating molecular building blocks of the same or the one or more different types to encourage growth of a macroscopic crystal,
wherein:
the mixing comprises introducing the tessellating molecular building blocks of the type with the additional tessellating molecular building blocks of the same or the one or more different types in a solution, and
the introducing comprises replacing the additional tessellating molecular building blocks of the same or the one or more different types with different additional tessellating molecular building blocks of the same or the one or more different types to encourage growth of a complex macroscopic crystal.

11. A method of assembling structural molecular building blocks into a macroscopic crystal, the method comprising:
forming multiple types of tessellating molecular building blocks,
each type of the tessellating molecular building blocks comprising first structural molecules arranged in a three-dimensional structure and second structural molecules,
wherein each of the second structural molecules is attached at a first region thereof to one of the first structural molecules and has a second region thereof for connection to a corresponding structural molecule of an additional tessellating molecular building block of a same or one or more different types; and
mixing the tessellating molecular building blocks of a type with additional tessellating molecular building blocks of the same or the one or more different types to encourage growth of a macroscopic crystal,
wherein:
the mixing comprises introducing the tessellating molecular building blocks of the type with the additional tessellating molecular building blocks of the same or the one or more different types in a solution, and the introducing comprises applying external forces to the solution to encourage growth of a complex macroscopic crystal.

12. A method of assembling structural molecular building blocks into a macroscopic crystal, the method comprising:

laying down a substrate comprising posts of structural molecules;

forming multiple types of tessellating molecular building blocks, each type of the tessellating molecular building blocks comprising first structural molecules arranged in a three-dimensional structure and second structural molecules, wherein each of the second structural molecules is attached at a first region thereof to one of the first structural molecules and has a second region thereof for connection to a post or to a corresponding structural molecule of an additional tessellating molecular building block of a same or one or more different types; and mixing the tessellating molecular building blocks of a type with the substrate and with additional tessellating molecular building blocks of the same or the one or more different types to encourage growth of a macroscopic crystal on the substrate.

13. The method according to claim 12, wherein:

the first and second structural molecules comprise at least one of DNA molecules, RNA molecules and elongate proteins, and the three-dimensional structure comprises at least one of a linear structure, an angular structure and a regular or irregular polygonal structure with at least length-wise and width-wise components respectively formed by the first structural molecules.

14. The method according to claim 12, wherein:

the first and second structural molecules comprise DNA molecules, and the three-dimensional structure comprises at least one of a linear structure, an angular structure and a regular or irregular polygonal structure with at least length-wise and width-wise components respectively formed by the first structural molecules.

15. The method according to claim 12, wherein the second structural molecules extend outwardly from the three-dimensional structure in one or more of first, second and third transverse dimensions and facilitate the tessellation of the tessellating molecular building blocks of the type with the additional tessellating molecular building blocks of the same or the one or more different types in the one or more of the first, second and third transverse dimensions.

16. The method according to claim 12, wherein the mixing comprises introducing the tessellating molecular building blocks of the type with the substrate and the additional tessellating molecular building blocks of the same or the one or more different types in a solution.

17. The method according to claim 16, wherein the introducing comprises replacing the additional tessellating molecular building blocks of the same or the one or more different types with different additional tessellating molecular building blocks of the same or the one or more different types to encourage growth of a complex macroscopic crystal on the substrate.

18. The method according to claim 16, wherein the introducing comprises applying external forces to the solution to encourage growth of a complex macroscopic crystal on the substrate.

19. The method according to claim 16, wherein the introducing comprises masking the substrate to encourage growth of a complex macroscopic crystal on the substrate.

20. The method according to claim 12, further comprising:

removing the macroscopic crystal from the substrate; and repeating the mixing to encourage growth of a second macroscopic crystal on the substrate.

* * * * *